(12) United States Patent
Barsoum et al.

(10) Patent No.: US 9,510,949 B2
(45) Date of Patent: Dec. 6, 2016

(54) PROSTHETIC JOINT COMPONENT WITH ROTATION-REGULATING STRUCTURE

(75) Inventors: Wael K. Barsoum, Bay Village, OH (US); Viktor E. Krebs, Rocky River, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 1409 days.

(21) Appl. No.: 12/823,818

(22) Filed: Jun. 25, 2010

(65) Prior Publication Data

US 2010/0331984 A1    Dec. 30, 2010

Related U.S. Application Data

(60) Provisional application No. 61/220,618, filed on Jun. 26, 2009.

(51) Int. Cl.
*A61F 2/32* (2006.01)
*A61F 2/30* (2006.01)
*A61F 2/36* (2006.01)

(52) U.S. Cl.
CPC .............. *A61F 2/30734* (2013.01); *A61F 2/36* (2013.01); *A61F 2/32* (2013.01); *A61F 2/3662* (2013.01); *A61F 2002/3037* (2013.01); *A61F 2002/3054* (2013.01); *A61F 2002/3055* (2013.01); *A61F 2002/30329* (2013.01); *A61F 2002/30332* (2013.01); *A61F 2002/30354* (2013.01); *A61F 2002/30362* (2013.01); *A61F 2002/30364* (2013.01); *A61F 2002/30365* (2013.01); *A61F 2002/30601* (2013.01); *A61F 2002/30649* (2013.01); *A61F 2002/30662* (2013.01); *A61F 2002/30738* (2013.01); *A61F 2002/3656* (2013.01); *A61F 2220/0033* (2013.01)

(58) Field of Classification Search
None
See application file for complete search history.

(56) References Cited

U.S. PATENT DOCUMENTS

| | | |
|---|---|---|
| 4,301,553 A | 11/1981 | Noiles |
| 4,538,305 A | 9/1985 | Engelbrecht et al. |
| 5,462,563 A | 10/1995 | Shearer et al. |
| 5,951,603 A * | 9/1999 | O'Neil et al. ............. 623/20.33 |
| 6,053,945 A | 4/2000 | O'Neil et al. |
| 6,773,461 B2 | 8/2004 | Meyers et al. |

(Continued)

OTHER PUBLICATIONS

"Impinge", English-Definition Dictionary, Reverso-Softissimo, date accessed Aug. 24, 2013.*

*Primary Examiner* — Yashita Sharma
*Assistant Examiner* — Rebecca Preston
(74) *Attorney, Agent, or Firm* — Tarolli, Sundheim, Covell & Tummino LLP (57) ABSTRACT

An elongate, longitudinally oriented outer sleeve includes an outer sleeve surface and has a sleeve body. A stem-receiving cavity extends from a distal sleeve end into the sleeve body. The distal sleeve end includes a sleeve interference protrusion extending from the distal sleeve end away from the sleeve body. A joint articulating member includes an elongate, longitudinally oriented stem. The joint articulating member includes a joint articulating surface spaced apart from a distal stem end by an angularly extending connector neck. When the stem is inserted into the stem-receiving cavity, the stem and the outer sleeve are configured for selective relative rotation about a shared longitudinal axis, and the connector neck impinges upon the sleeve interference protrusion responsive to a predetermined amount of relative rotation between the stem and the outer sleeve to prevent relative rotation between the stem and the outer sleeve outside a predetermined range of allowable rotation.

22 Claims, 7 Drawing Sheets

(56) References Cited

U.S. PATENT DOCUMENTS 6,972,039 B2 * 12/2005 Metzger et al. ........... 623/20.29
7,291,174 B2 * 11/2007 German et al. ............ 623/20.15
2008/0114464 A1 * 5/2008 Barnett et al. ............. 623/20.33

* cited by examiner

PROSTHETIC JOINT COMPONENT WITH ROTATION-REGULATING STRUCTURE

RELATED APPLICATION

This application claims priority from U.S. Provisional Application No. 61/220,618, filed Jun. 26, 2009, the subject matter of which is incorporated herein by reference.

TECHNICAL FIELD

The present invention relates to an apparatus and method for use of a prosthetic joint component and, more particularly, to regulating rotation of a prosthetic joint component.

BACKGROUND OF THE INVENTION

It is known that permanent reconstruction of a bone joint which has been malformed from birth, or as a result of disease, or accidental injury, may be achieved by the substitution of the afflicted portion(s) of the joint by an artificial implant constructed of a biocompatible material. It is desirable that any replacement joint should imitate the natural articulation of the healthy joint.

One method of replacing the hip joint involves the use of a stemmed femoral prosthesis adapted to be inserted and retained within the medullary canal of the femur after removal of the natural femoral head. The socket function of the replacement joint is performed by an acetabular cup implant which defines a spherical recess adapted to receive the ball end of the femoral prosthesis. Dislocation of the femoral ball is prevented by the soft tissue structures and the natural stability of the spherical recess. However, it is possible for the femoral head to be removed from the acetabulum, thus causing a dislocation for various reasons including impingement, soft tissue laxity, or component malposition.

Most known hip prostheses require both the femoral and acetabular components to be fixed rigidly into their corresponding bones, either by a tight press-fit, cemented, or screw attachment. Without the ability to rotate the femur around its longitudinal axis in a controlled manner, due to muscle configuration and surrounding tissue, impingement of known types of hip prostheses is easily possible. Known hip implants include range-of-motion regions posing the danger of aggressive dislocation (by leverage) or implant damage if the femur were to be rotated into an unsuitable orientation.

SUMMARY OF THE INVENTION

In an embodiment of the present invention, a prosthetic joint component is described. An elongate, longitudinally oriented outer sleeve includes an outer sleeve surface configured for implantation into native bone and has a sleeve body extending between longitudinally separated proximal and distal sleeve ends. A stem-receiving cavity extends from the distal sleeve end into the sleeve body substantially in a first longitudinal direction. The distal sleeve end includes a sleeve interference protrusion extending from the distal sleeve end away from the sleeve body substantially in a second longitudinal direction opposite the first longitudinal direction. A joint articulating member includes an elongate, longitudinally oriented stem with longitudinally spaced proximal and distal stem ends separated by a stem body. The proximal stem end is configured for selective insertion into the stem-receiving cavity. The joint articulating member includes a joint articulating surface spaced apart from the distal stem end by an angularly extending connector neck. When the stem is inserted into the stem-receiving cavity, the stem and the outer sleeve are configured for selective relative rotation about a shared longitudinal axis, and the connector neck impinges upon the sleeve interference protrusion responsive to a predetermined amount of relative rotation between the stem and the outer sleeve to prevent relative rotation between the stem and the outer sleeve outside a predetermined range of allowable rotation.

In an embodiment of the present invention, a prosthetic joint component is described. A joint articulating member includes a joint articulating surface. An anchor member is configured for implantation into a native bone. A chosen one of the joint articulating member and the anchor member includes a stem. The stem is configured for insertion into a stem-receiving cavity in the other one of the joint articulating member and the anchor member. At least one of the joint articulating member and the anchor member includes a sleeve interference projection extending therefrom. When the stem is inserted into the stem-receiving cavity, the joint articulating member and the anchor member are configured for selective relative rotation about a shared longitudinal axis, a portion of at least one of the joint articulating member and the anchor member impinges upon the sleeve interference protrusion responsive to a predetermined amount of relative rotation between the joint articulating member and the anchor member to prevent relative rotation between the joint articulating member and the anchor member outside a predetermined range of allowable rotation.

In an embodiment of the present invention, a method of regulating rotation of a prosthetic joint component is described. An elongate, longitudinally oriented outer sleeve including an outer sleeve surface configured for implantation into native bone and having a sleeve body extending between longitudinally separated proximal and distal sleeve ends is provided. A stem-receiving cavity extends from the distal sleeve end into the sleeve body substantially in a first longitudinal direction. The distal sleeve end includes a sleeve interference protrusion extending from the distal sleeve end away from the sleeve body substantially in a second longitudinal direction opposite the first longitudinal direction. A joint articulating member including an elongate, longitudinally oriented stem with longitudinally spaced proximal and distal stem ends separated by a stem body is provided. The proximal stem end is configured for selective insertion into the stem-receiving cavity. The joint articulating member includes a joint articulating surface spaced apart from the distal stem end by an angularly extending connector neck. At least a portion of the stem is inserted into the stem-receiving cavity. The stem and the outer sleeve are relatively rotated about a shared longitudinal axis. The connector neck impinges upon the sleeve interference protrusion responsive to a predetermined amount of relative rotation between the stem and the outer sleeve. Relative rotation between the stem and the outer sleeve outside a predetermined range of allowable rotation is prevented.

BRIEF DESCRIPTION OF THE DRAWINGS

For a better understanding of the invention, reference may be made to the accompanying drawings, in which.

DESCRIPTION OF EMBODIMENTS

Figure 1:
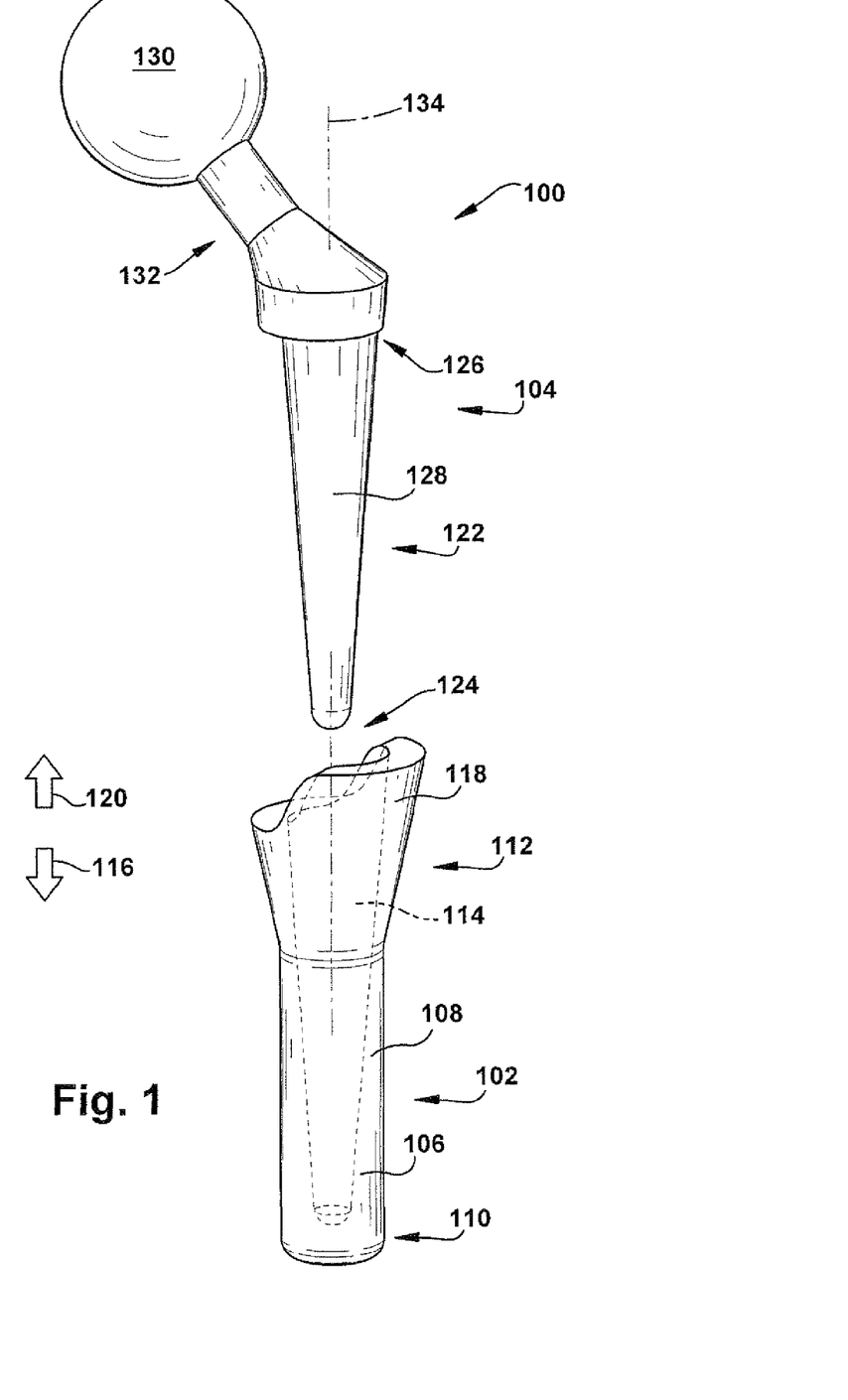
FIG. 1 is an exploded perspective view of an embodiment of the present invention.

In accordance with a first embodiment of the present invention, FIG. 1 depicts a prosthetic joint component 100 including an elongate, longitudinally oriented anchor member, described herein as an outer sleeve 102, and a joint articulating member 104. The outer sleeve 102 includes an outer sleeve surface 106 configured for implantation into native bone. The outer sleeve 102 has a sleeve body 108 extending between longitudinally separated proximal and distal sleeve ends 110 and 112, respectively. A stem-receiving cavity 114 extends from the distal sleeve end 112 into the sleeve body 108 substantially in a first longitudinal direction 116. The distal sleeve end 112 includes a sleeve interference protrusion 118 extending from the distal sleeve end 112 away from the sleeve body 108 substantially in a second longitudinal direction 120 opposite the first longitudinal direction 116.

The joint articulating member 104 includes an elongate, longitudinally oriented stem 122 with longitudinally spaced proximal and distal stem ends 124 and 126, respectively, separated by a stem body 128. The proximal stem end 124 is configured for selective insertion into the stem-receiving cavity 114 of the outer sleeve 102. The joint articulating member 104 includes a joint articulating surface 130 spaced apart from the distal stem end 126 by an angularly extending connector neck 132. "Angularly extending" is used here to indicate that the connector neck 132 is oriented to hold at least a portion of the joint articulating surface 130 in a laterally spaced relationship with a longitudinal axis 134 defined, at least in part, by the stem 122. As shown here, the connector neck 132 may include a plurality of differently shaped segments. The term "connector neck" is used herein to collectively reference any structure(s), or portions thereof, extending between the joint articulating surface 130 and the distal stem end 126.

The joint articulating surface 130 is shown as a spherical structure for use in a ball-and-socket joint; for example, in a traditional or inverted hip or shoulder prosthesis. However, the joint articulating surface 130 may have any suitable shape, size, orientation, configuration, or other property and may form a portion of at least one of a prosthetic hip joint, a prosthetic shoulder joint, a prosthetic ankle joint, a prosthetic knee joint, a prosthetic elbow joint, a prosthetic wrist joint, a prosthetic finger joint, a prosthetic toe joint, and a prosthetic spine component. For example, and depending upon the use environment, the articulating surface may be at least one of convex and concave. All or only a portion of the joint articulating surface 130, such as a segment of the spherical articulating surface of the Figures, might be used to contact other prosthesis components in a particular application of the present invention.

Figure 2:
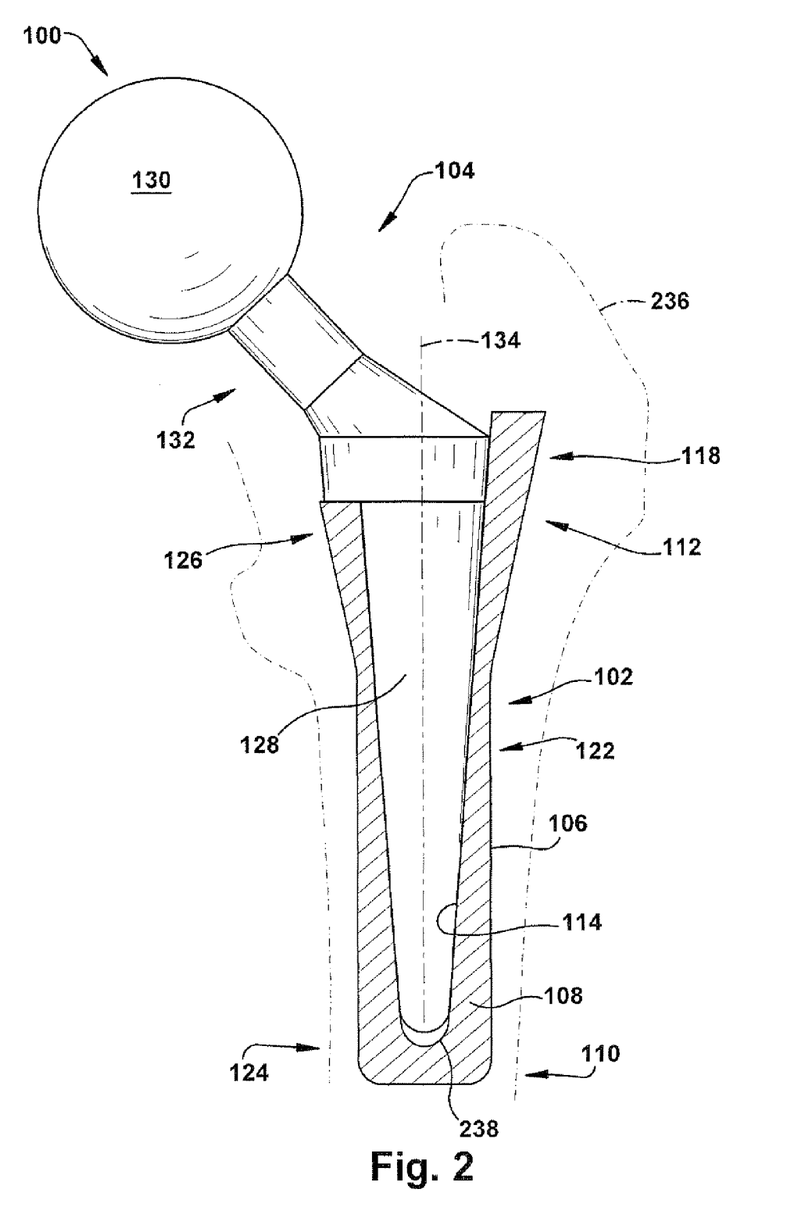
FIG. 2 is a partial cross-sectional view of the embodiment of FIG. 1 in a use environment in a first orientation.

FIG. 2 is a partial cutaway view with the multi-piece prosthetic joint component 100 depicted in an installed position within a native bone, shown in dashed line at 236, of the patient. Because the depicted multi-piece prosthetic joint component 100 of FIG. 2 is an elongate-stemmed component of a ball-and-socket joint, the bone 236 is shown as a femur in this example embodiment. One of ordinary skill in the art can readily provide a prosthetic joint component 100 for a particular application of the present invention, however, regardless of the prosthesis location.

In FIG. 2, the outer sleeve 102 has been affixed into a native bone 236, such as, but not limited to, the native femur bone shown and described herein. This can be accomplished in any suitable manner. For example, the outer sleeve 102 can be affixed within an existing or created void in the bone 236 via any one or combination of adhesion, cementing, bone in-growth to a porous outer sleeve surface 106, frictional engagement (possibly augmented with a fluted or splined outer sleeve surface), pinning via a through-extending rod or screw, or any other suitable attachment mechanisms or techniques. The outer sleeve 102 need not be permanently affixed into the bone 236 before complete installation of the multi-piece prosthetic joint component, particularly in the case of a lengthy attachment process such as bone in-growth.

In FIG. 2, the stem 122 is fully inserted into the stem-receiving cavity 114. It is contemplated, however, that in certain embodiments (not shown), the proximal stem end 124 and a proximal cavity end 238 of the stem-receiving cavity 114 may have a longitudinal space therebetween due to a partial insertion of the stem 122 into the stem-receiving cavity. One of ordinary skill in the art can readily provide a structure or other means, located at any suitable position on a structure of the prosthetic joint component 100, to separate the proximal sleeve rim 110 and the interface rim 126 in the initial orientation, when desired. The partial insertion could also or instead be effected by the relative lengths of the stem 122 and the stem-receiving cavity 114; when the former is shorter than the latter, there will be a longitudinal space therebetween.

Figure 3A:
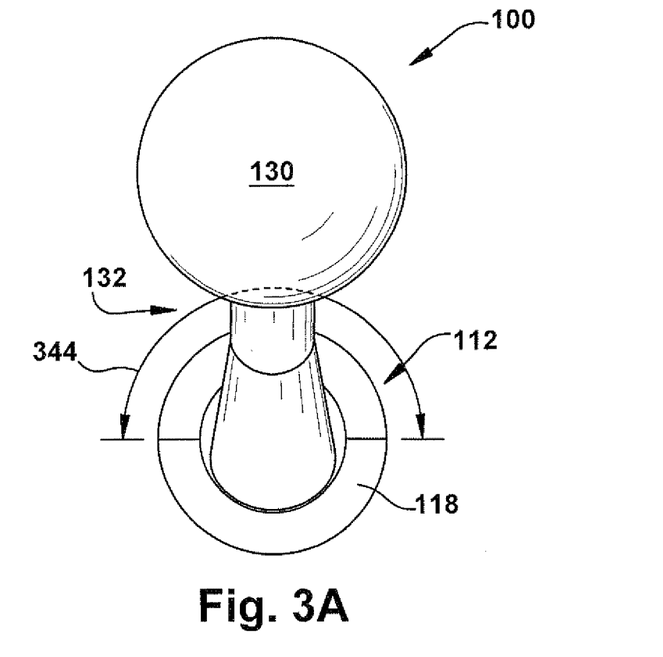
FIG. 3A is a partial top view of the embodiment of FIG. 2 in the first orientation.
Figure 3B:
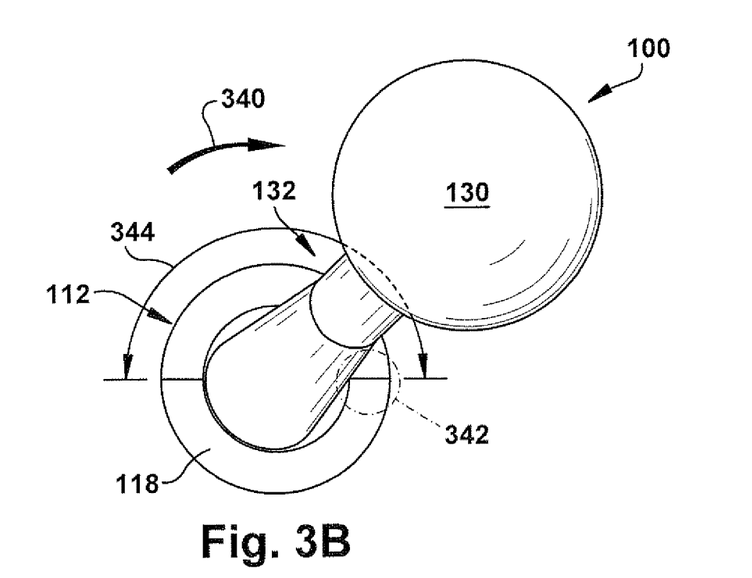
FIG. 3B is a partial top view of the embodiment of FIG. 1 in a second orientation.

FIGS. 3A and 3B are partial top views of the prosthetic joint component 100 in first and second orientations, respectively. In FIG. 3A, the prosthetic joint component 100 is arranged similarly to the first orientation configuration of FIG. 2, with the stem 122 inserted into the outer sleeve 102 and the connector neck 132 radially spaced apart from the sleeve interference protrusion 118. To achieve the position shown in FIG. 3B, the stem 122 and the stem-receiving cavity 114 are relatively rotated from the FIG. 3A orientation about a shared longitudinal axis 134 (as indicated by radial arrow 340). This relative rotation may be caused in any manner, and by any suitable amount of movement of either or both of the outer sleeve 102 and the joint articulating member 104 in an absolute frame of reference. For example, the joint articulating surface 130 may mate with a socket prosthetic member (not shown) implanted in an adjacent bone (not shown), and the joint articulating member 104 could be rotated by a force transferred from that socket prosthetic member. As another example, the native bone 236 could be rotated by the patient (e.g., by swinging the leg when the prosthetic joint component 100 is part of a prosthetic hip joint), which could rotate the outer sleeve 102 relative to the joint articulating member 104.

Regardless of the way that the relative rotation is produced, the connector neck 132 is shown in FIG. 3B as impinging upon the sleeve interface projection 118 at an impingement area (circled generally at 342). This impingement occurs responsive to a predetermined amount of relative rotation between the stem 122 and the outer sleeve 102 and is operative to substantially prevent relative rotation between the stem and the outer sleeve outside a predetermined range of allowable rotation. In this manner, the relative rotation between the stem 122 and the outer sleeve 102 can be at least partially prevented from becoming an unrestricted 360° turn. One of ordinary skill in the art will realize that this impingement area 342 feature may supplement or supplant the rotation-restricting functions of any nearby body tissues (not shown). These nearby body tissues normally would help to statically or dynamically restrain undesired motion of the joint, but may be damaged or destroyed during the joint replacement procedure.

Any portion of the connector neck 132 may impingingly contact the sleeve interference protrusion 118 to prevent further relative rotation of the stem 122 and the outer sleeve 102 in the radial direction 340 (clockwise, in the orientation of FIGS. 3A and 3B) or in a turn direction opposite the radial direction (here, counterclockwise). More broadly, it is contemplated that any structure of the stem 122 could impingingly contact any structure of the outer sleeve 102 to provide the described rotational restraint.

As can be seen in the top view of FIG. 3A, at least one sleeve interference protrusion 118 defines a radially oriented allowable rotation region 344 longitudinally adjacent to the distal sleeve end 112; that is, extending out of the plane of the page in FIG. 3A. The allowable rotation region 344 is a two- or three-dimensional space within which a chosen structure of the joint articulating member 104 is permitted to move without restriction arising from impingement of the stem 122 and the outer sleeve 102 at the impingement area 342. In these Figures, the chosen structure of the joint articulating member 104 is the connector neck 132, but it is contemplated that the chosen structure for which the allowable rotation region 344 is provided may be the joint articulating surface 130, the stem body 128, or any other structure of the joint articulating member 104. The allowable rotation region 344 in these Figures, based on the connector neck 132, is accordingly the area radially adjacent an area of the distal sleeve end 112 from which the sleeve interference protrusion 118 does not extend.

One of ordinary skill in the art will recognize that a desired allowable rotation region 344 will be dependent upon the final implantation position of the prosthetic joint component 100, the configuration of the prosthetic joint component, and the offset angle and distance of the relevant area of the joint articulating surface 130 from the distal sleeve end 112. That person of ordinary skill in the art will therefore be able to provide a suitable sleeve interference protrusion 118 to define an appropriate allowable rotation region 344 for a particular application of the present invention. As shown in FIGS. 3A and 3B, the sleeve interference protrusion 118 extends longitudinally (out of the plane of the page in FIGS. 3A and 3B) from approximately half of a circumference of the distal sleeve end 112, for ease of depiction. However, the sleeve interference protrusion 118 may extend longitudinally from any amount of the distal sleeve end 112, including a majority of the circumference and a minority of the circumference. The sleeve interference protrusion 118 may have any suitable size, shape, thickness, location, configuration, or other properties as desired for a particular application of the present invention.

The sleeve interference protrusion 118 could be a slim, spike-like protuberance or could be a near-complete cylindrical structure about the circumference of the distal sleeve end 112 as appropriate to provide the desired allowable rotation region 344. The interface between the sleeve interference protrusion 118 and a remaining circumference of the distal sleeve end 112, as well as any other portion of the sleeve interference protrusion, may be filleted, beveled, or chamfered, as shown in the Figures, to avoid presenting a sharp corner to adjacent body structures. The more of the distal sleeve end 112 from which the sleeve interference protrusion 118 extends longitudinally, the smaller the resulting allowable rotation region. The allowable rotation region 344 defines the predetermined range of allowable rotation within which relative rotation between the stem 122 and the outer sleeve 102 is permitted. The range of allowable rotation may be positioned in any suitable area around the circumference of the distal sleeve end 112, for any desired orientation with respect to the native bone 236 when the outer sleeve 102 is implanted into the patient. The range of allowable rotation may be in the range of between about 30° and 60°, for example, of a full relative rotation of the stem 122 and the outer sleeve 102 in a typical prosthetic joint component 100 for a replacement hip joint. The joint articulating member 104 may be oriented in any suitable position within the range of allowable rotation when the prosthetic joint component 100 is in an initial or resting position; it is contemplated that the prosthetic joint component 100 may be designed to place the connector neck 132 either substantially in the center of the range of allowable rotation or in a biased position toward either side of the range of allowable rotation.

In FIG. 3B, the stem 122 and outer sleeve 102 have been relatively rotated in the radial direction 340 into the second orientation, to bring the connector neck 132 into impinging contact with the sleeve interference protrusion 118 at the impingement area 342. Therefore, the stem 122 and outer sleeve 102 are constrained from further relative rotation in the radial direction 340. Regardless of which structures of the outer sleeve 102 and the joint articulating member 104 come into contact at the impingement area 342, those structures may be shaped, padded, reinforced, or otherwise designed specifically to withstand repeated contacts of the force, nature, and frequency expected to be encountered in a particular application of the present invention. It should also be understood that the impingement area 342 is an approximately indicated region and that the portions of the outer sleeve 102 and the joint articulating member 104 which actually come into mutual contact may vary from one prosthetic joint component 100 to another, or even from time to time in the same prosthetic joint component.

FIGS. 4-6B depict a prosthetic joint component 100 according to a second embodiment of the present invention. The prosthetic joint component 100' of FIGS. 4-6B is similar to the prosthetic joint component 100 of FIGS. 1-3B and therefore, structures of FIGS. 4-6B that are the same as or similar to those described with reference to FIGS. 4-6B have the same reference numbers with the addition of a "prime" mark. Description of common elements and operation similar to those in the previously described first embodiment will not be repeated with respect to the second embodiment.

The prosthetic joint component 100' of FIGS. 4-6B differs from that of the first embodiment in the configuration of the sleeve interference protrusion 118'. In the prosthetic joint component 100' of the second embodiment, the sleeve interference protrusion 118' extends from the distal sleeve end 112 at a more gradual angle than does that of the first embodiment. Accordingly, the impingement of the connector neck 132' and the sleeve interference protrusion 118' occurs in a moderated manner such that the connector neck travels along the sleeve interference protrusion for a time before the contact therebetween prevents further relative rotation between the stem 122' and the outer sleeve 102'. In order to provide this feature, the sleeve interference protrusion 118' defines at least one radially oriented altered rotation region 546 longitudinally adjacent to the distal sleeve end 112' and radially adjacent to the allowable rotation region 344'. The altered rotation region 546 defines a predetermined range of altered rotation in a similar manner to that in which the allowable rotation region 344' defines the predetermined range of allowable rotation. Two altered rotation ranges 546 are shown in the Figures, one on either side of the allowable rotation region 344', but any number of altered rotation ranges may be present for a particular application of the present invention.

Figure 4:
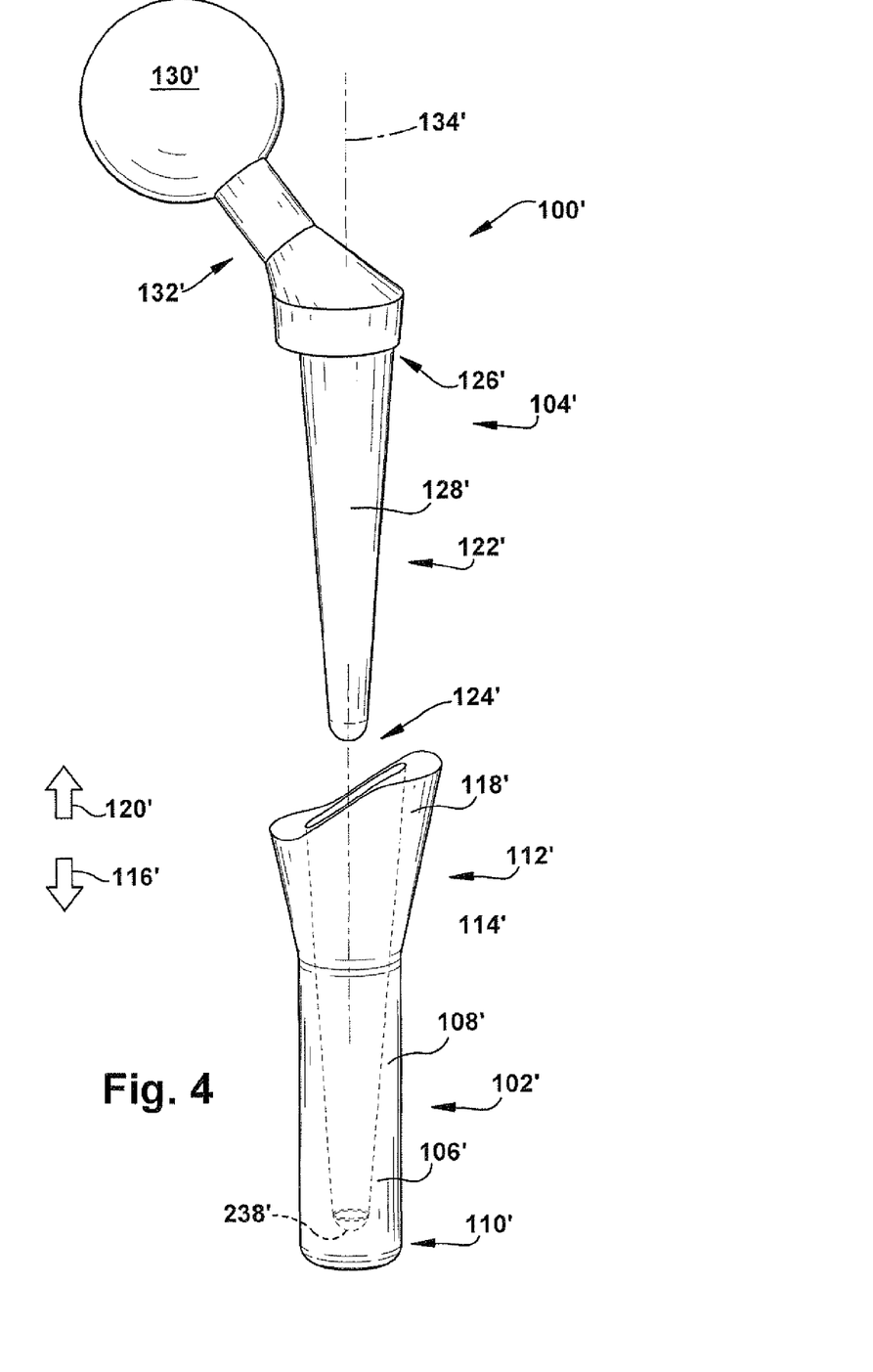
FIG. 4 is an exploded perspective view of an embodiment of the present invention.

When the connector neck 132' is moving radially within the altered rotation region 546, the connector neck is in sliding contact with the sleeve interference protrusion 118' and relative rotation therebetween is not prevented. However, the motion of the stem 122' relative to the outer sleeve 102' during this sliding contact is longitudinally altered because the connector neck 132' "rides up" the sleeve interference protrusion 118' to at least partially withdraw the stem from the stem-receiving cavity 114'. In other words, the connector neck 132' impinges upon the sleeve interference protrusion 118' responsive to a predetermined amount of relative rotation between the stem 122' and the outer sleeve 102' to alter longitudinal insertion of the stem into the outer sleeve when the relative rotation between the stem and the outer sleeve is within a predetermined range of altered rotation.

Figures 5A, 5B, 5C:
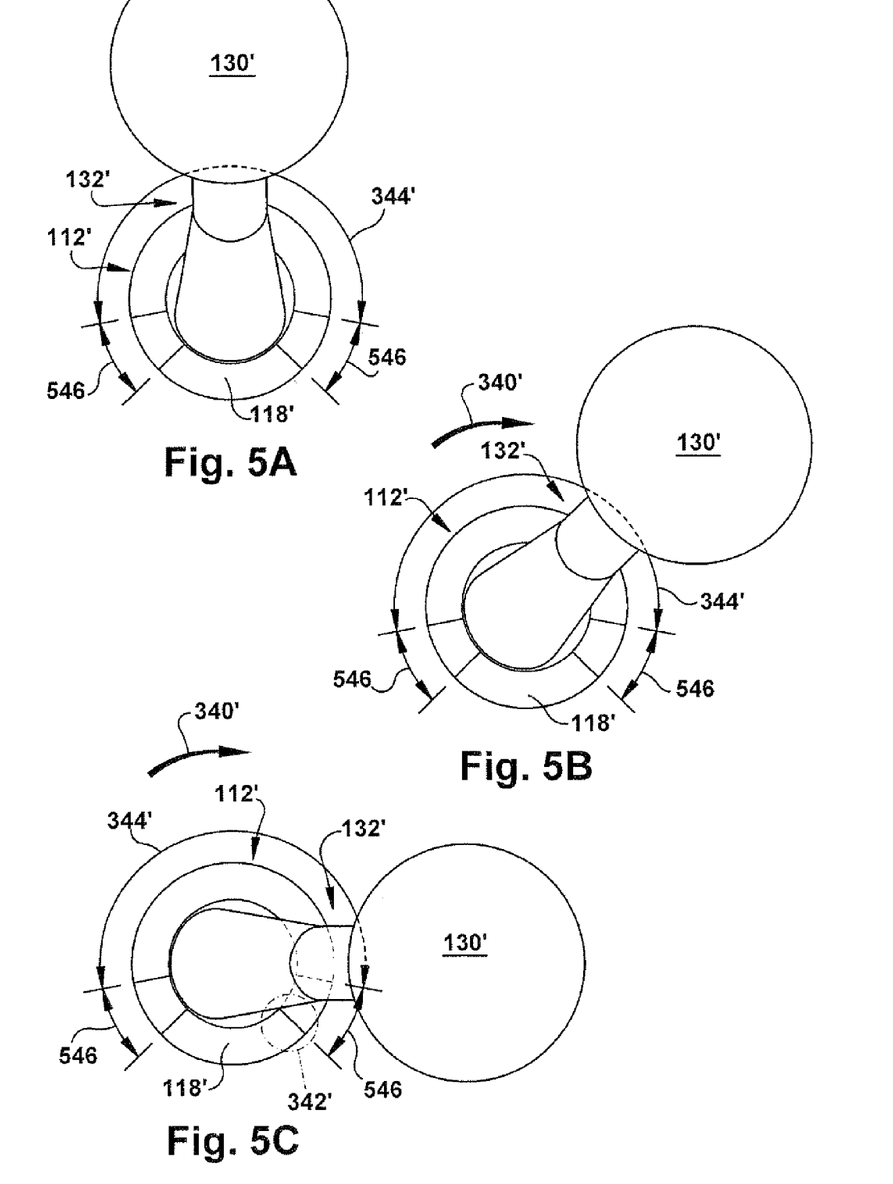
FIG. 5A is a partial top view of the embodiment of FIG. 4 in a first orientation.
FIG. 5B is a partial top view of the embodiment of FIG. 4 in a second orientation.
FIG. 5C is a partial top view of the embodiment of FIG. 4 in a third orientation.
Figure 6A:
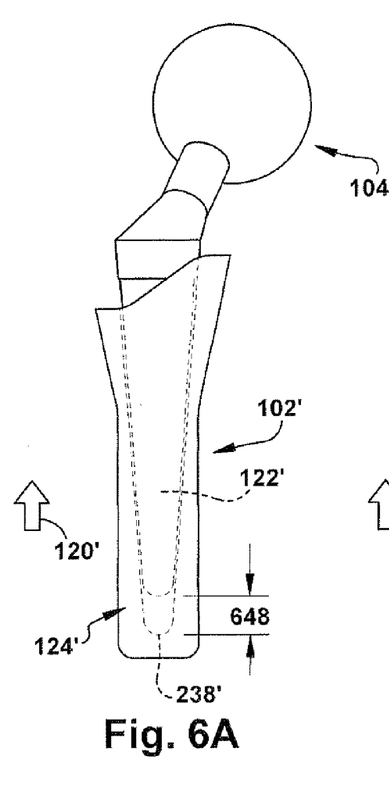
FIG. 6A is a schematic side view of the embodiment of FIG. 4 in the second orientation.
Figure 6B:
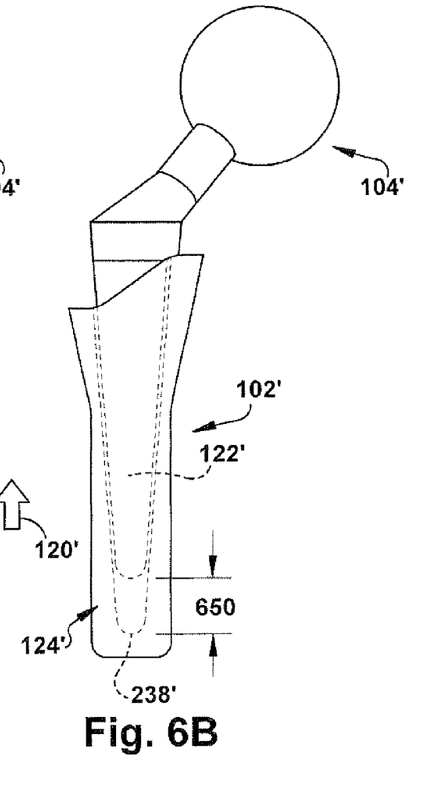
FIG. 6B is a schematic side view of the embodiment of FIG. 4 in the third orientation.

This longitudinal expansion is shown in the sequence of FIGS. 6A-6B, which correspond to the rotational positions of the prosthetic joint component 100' in FIGS. 5B and 5C, respectively. Here, the stem 122' is presumed to be substantially fully inserted into the stem-receiving cavity 114' (with the proximal stem end 124' being located at or closely adjacent the proximal cavity end 238', similar to the FIG. 2 depiction of the first embodiment) when the relative rotation between the stem and the outer sleeve 102' is within the predetermined range of allowable rotation corresponding to the allowable rotation region 344'. In the first (rotational) orientation shown in FIG. 5A, the connector neck 132' is located within the allowable rotation region 344' and, absent a retarding or damping structure (not shown), the stem 122' and outer sleeve 102' may freely rotate relative to one another. The rotation referenced in the below discussion of the sequence of FIGS. 5A-5C will be presumed to be occurring in the direction of the radial arrow 340'.

As the stem 122' and outer sleeve 102' rotate sufficiently to bring the connector neck 132' into initial sliding contact with the sleeve interference protrusion 118', the connector neck 132' transitions into the altered rotation region 546, shown in the second orientation of FIG. 5B. As the stem 122' and outer sleeve 102' continue to rotate past that initial contact, the connector neck 132' climbs longitudinally up (i.e., in the second longitudinal direction 120') the sleeve interference protrusion 118' and pulls a portion of the stem 122' longitudinally out of the stem-receiving cavity 114'. The prosthetic joint component 100' thus becomes longitudinally expanded, as shown in FIG. 6A.

"Riding up" of the connector neck 132' on the sleeve interference protrusion 118' causes a first separation distance 648 to become interposed between the proximal stem end 124' and the proximal cavity end 238' within the stem-receiving cavity 114'. This first separation distance 648 may be a total distance between the proximal stem end 124' and the proximal cavity end 238', as shown in FIG. 6A, when the proximal stem end and the proximal cavity end are in contact while the connector neck 132' is rotating in the allowable rotation region 344, or the first separation distance may be an additional distance when the proximal stem end and the proximal cavity end are already longitudinally separated while the connector neck is rotating in the allowable rotation region.

In essence, the sleeve interference protrusion 118' of the second embodiment is structured such that initial radially-oriented contact between the connector neck 132' and the sleeve interference protrusion does not result in the connector neck "hitting a wall" at an impingement area 342'. Instead, the portion of the sleeve interference protrusion 118' initially contacts the connector neck 132' in an obliquely angled relationship which permits continued radial motion of the connector neck relative to the sleeve interference protrusion while imparting a degree of longitudinal motion where the connector neck is urged up the slope of that portion of the sleeve interference protrusion.

When the stem 122' has rotated a sufficient amount relative to the outer sleeve 102' to bring the prosthetic joint component 100' from the second orientation of FIG. 2 into the third orientation of FIG. 5C, the connector neck 132' has reached the end of the altered rotation region 546 and contacts the sleeve interference protrusion 118' at the impingement area 342'. This impingement prevents further rotation of the stem 122' in the direction of the radial arrow 340' and therefore binds the prosthetic joint component 100' in a similar manner to that of the first embodiment.

At the point that the connector neck 132' contacts the sleeve interference protrusion 118' at the impingement area 342', the longitudinal separation of the proximal stem end 124' and the proximal cavity end 238' within the stem-receiving cavity 114' reaches a second separation distance 650, as shown in FIG. 6B. This second separation distance 650 will normally be larger than the first separation distance 648, but one of ordinary skill in the art can readily shape the sleeve interference protrusion 118' to "tune" the distance between the proximal stem end 124' and the proximal cavity end 238' at various points corresponding to the radial position of the connector neck 132' relative to the sleeve interference protrusion. For example, a longitudinal dip or scoop (not shown) could be provided in the sleeve interference protrusion 118' to create a detent function which slightly reduces the distance between the proximal stem end 124' and the proximal cavity end 238' when the stem 122' is prevented from further relative rotation with respect to the outer sleeve 102'. In the depicted second embodiment of the prosthetic joint component 100', however, the distance between the proximal stem end 124' and the proximal cavity end 238' will bear a substantially linear relationship to the radial position of the connector neck 132' in the altered rotation region 546.

In any embodiment of the present invention, it is contemplated that the stem 122 and the outer sleeve 102 may rotate freely within the predetermined ranges of allowable and altered rotation. Alternately, relative rotation between the stem 122 and the outer sleeve 102 could be controlled by at least one rotation detent structure (not shown), such as, but not limited to, a series of notches or depressions in one or both of the distal sleeve end 112 and the joint articulating member 104, a ratchet mechanism, a spring mechanism, or any other suitable retarding structure or mechanism.

It is also contemplated that the longitudinal relationship between the proximal stem end 124' and the proximal cavity end 238' in the second embodiment (i.e., the amount of longitudinal expansion of the prosthetic joint component 100') could be controlled selectively by at least one longitudinal variance controlling structure (not shown), such as, but not limited to, a constraining member preventing loss of contact between the connector neck 132' and the sleeve interference protrusion 118', a friction-controlled or friction-reduced surface on one or more of the proximal sleeve rim and the interface rim, a control sleeve (not shown) surrounding the interface between the outer sleeve and the joint articulating member, or any other suitable constraining structure or mechanism. For example, the longitudinal relationship between the proximal stem end 124' and the proximal cavity end 238' could be controlled selectively by controlling an extent to which the stem 122' is inserted into the stem-receiving cavity 114', perhaps by, e.g., a filler material (not shown) placed into the stem-receiving cavity before insertion of the stem, or in any other suitable manner.

Additionally or alternatively, a rate of relative rotation between the stem 122 and the outer sleeve 102 could be adjusted and/or controlled through the structure of the sleeve interference protrusion 118 and/or the connector neck 132. For example, the profile of the sleeve interference protrusion 118 and/or the connector neck 132 could be chosen to provide a geometry which varies the amount of force needed to provide the described longitudinal expansion in a linear or nonlinear manner as the amount of relative rotation between the stem 122 and the outer sleeve 102 changes.

Moreover, it is contemplated that one or both of the connector neck 132 and sleeve interference protrusion 118 may include an interlocking structure (not shown) which selectively restrains the outer sleeve 102 and joint articulating member 104 from complete disengagement. Optionally, such an interlocking structure (or structures), when present, will allow for some degree of longitudinal separation between the proximal stem end 124 and the proximal cavity end 238 while preventing the stem 122 from being substantially withdrawn from the stem-receiving cavity 114.

Figure 7:
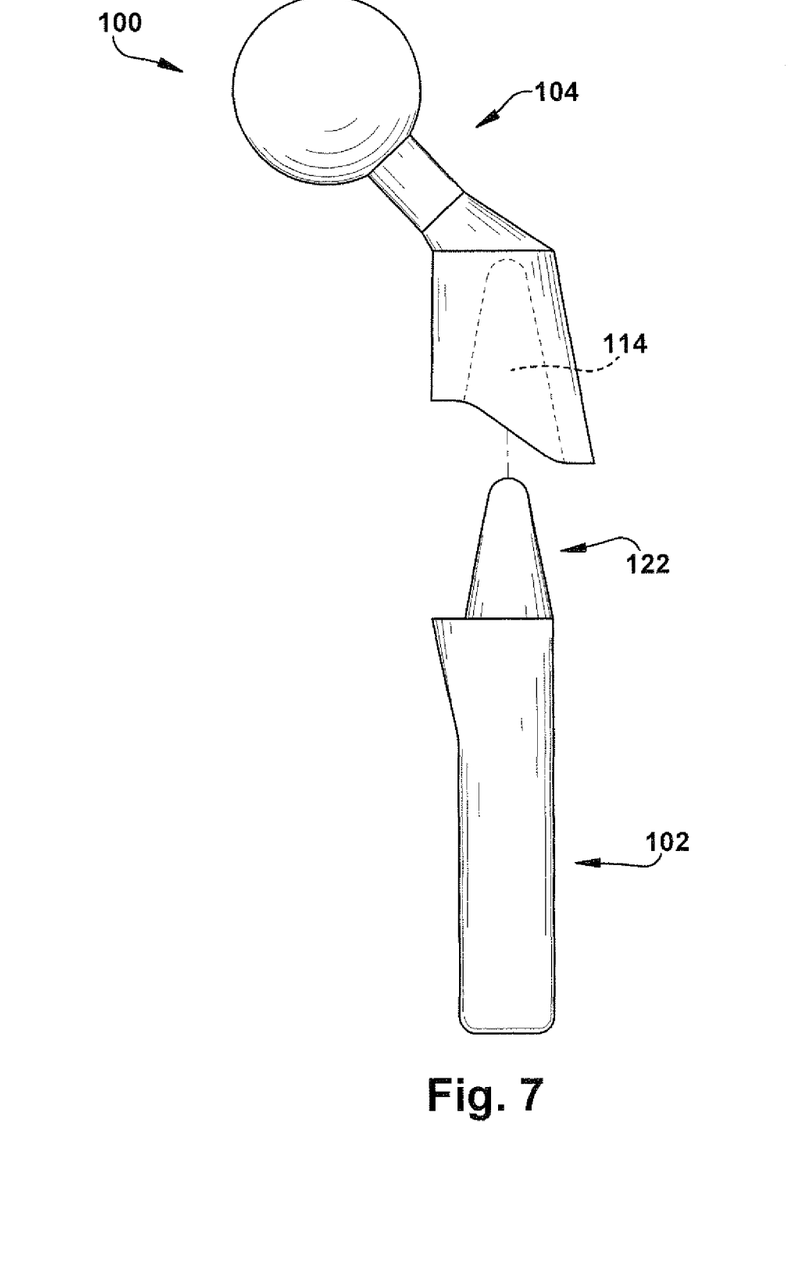
FIG. 7 is an exploded perspective view of an alternative configuration of the embodiment of FIG. 1.

It is contemplated, too, that the outer sleeve 102 (acting in this example as a positive-space anchor member, not a negative-space sleeve) may include the stem 122, and that the stem 122 would be configured for insertion into a stem-receiving cavity 114 in the joint articulating member 104, as shown in FIG. 7. With this reversed male/female relationship between the outer sleeve 102 and the joint articulating member 104, a differently configured prosthetic joint component 100 than that shown in FIGS. 1-6B can be provided, which may be desirable for a particular application of the present invention.

Finally, it is contemplated that one or both of the joint articulating member 104 and the outer sleeve 102 may include a sleeve interference projection 118 extending therefrom. Accordingly, a portion of at least one of the joint articulating member 104 and the anchor member 102 will then impinge upon the sleeve interference projection(s) 118 responsive to the predetermined amount of relative rotation between the joint articulating member and the anchor member to prevent relative rotation between the joint articulating member and the anchor member outside the predetermined range of allowable rotation.

While aspects of the present invention have been particularly shown and described with reference to the preferred embodiment above, it will be understood by those of ordinary skill in the art that various additional embodiments may be contemplated without departing from the spirit and scope of the present invention. For example, any of the structures discussed could be manufactured from component parts or integrally formed. The specific method described above for installing the multi-piece prosthetic joint component 100 is merely illustrative; one of ordinary skill in the art could readily determine any number of tools, sequences of steps, or other means/options for placing the apparatus, or components thereof, into positions substantively similar to those shown and described herein. Any of the described structures and components could be integrally formed or separately provided of any suitable material or combinations of materials; however, the chosen material(s) should be biocompatible for most applications of the present invention. Though certain components described herein are shown as having specific geometric shapes (e.g., the spherical articulating surface 130), all structures of the present invention may have any suitable shapes, sizes, configurations, relative relationships, cross-sectional areas, or any other physical characteristics as desirable for a particular application of the present invention. A description of a "radial" direction or orientation with reference to a curvilinear structure should be interpreted as meaning an analogous feature or direction for a structure which includes non-curvilinear portions. Neither the stem 122 nor the outer sleeve 102, nor any other component or structure of the multi-piece prosthetic joint component, is necessarily symmetrical across any particular plane, even if depicted as such herein. A sleeve liner (not shown) may be located within at least a portion of the stem-receiving cavity 114 and provide frictional, antibacterial, or other functions to the stem 122 to stem-receiving cavity interface; cross-linked polyethylene may be a suitable material for a sleeve liner in a particular application of the present invention. A frictional alteration structure, such as, but not limited to, a bearing or damper, may be provided to assist in controlling rotation between the stem 122 and outer sleeve 102. The impingement area 342, which is created when the joint articulating member 104 is prevented from further radial rotation relative to the outer sleeve 102, may be a location of application of forces in the radial direction, longitudinal direction, or any other desired directions or combinations of directions. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, we claim:

1. A prosthetic joint component, comprising:
    an elongate, longitudinally oriented outer sleeve including an outer sleeve surface configured for implantation into native bone of a patient and having a sleeve body extending between longitudinally separated proximal and distal sleeve ends, a stem-receiving cavity extending from the distal sleeve end into the sleeve body substantially in a first longitudinal direction, the sleeve including a sleeve interference protrusion extending from the distal sleeve end away from the sleeve body substantially in a second longitudinal direction opposite the first longitudinal direction; and
    a joint articulating member including an elongate, longitudinally oriented stem with longitudinally spaced proximal and distal stem ends separated by a stem body, the proximal stem end being configured for selective insertion into the stem-receiving cavity, the joint articulating member including a joint articulating surface spaced apart from the distal stem end by an angularly extending connector neck; wherein when the stem is inserted into the stem-receiving cavity with the outer sleeve and joint articulating member implanted within the patient's body, the stem and the outer sleeve are configured for selective relative rotation, impelled by action of the patient, about a shared longitudinal axis, and the connector neck impinges upon the sleeve interference protrusion responsive to a predetermined amount of relative rotation between the stem and the outer sleeve to prevent relative rotation between the stem and the outer sleeve outside a predetermined range of allowable rotation.

2. The prosthetic joint component of claim 1, wherein the joint articulating surface forms a portion of at least one of a prosthetic hip joint, a prosthetic shoulder joint, a prosthetic ankle joint, a prosthetic knee joint, a prosthetic elbow joint, a prosthetic wrist joint, a prosthetic finger joint, a prosthetic toe joint, and a prosthetic spine component.

3. The prosthetic joint component of claim 1, wherein the sleeve interference protrusion extends longitudinally from a majority of the distal sleeve end.

4. The prosthetic joint component of claim 1, wherein the sleeve interference protrusion defines a radially oriented allowable rotation region longitudinally adjacent to the distal sleeve end, the allowable rotation region defining the predetermined range of allowable rotation.

5. The prosthetic joint component of claim 1, wherein the predetermined range of allowable rotation is in the range of 30-60° of a full 360° relative rotation of the stem and the outer sleeve.

6. The prosthetic joint component of claim 1, wherein the connector neck impinges upon the sleeve interference protrusion responsive to a predetermined amount of relative rotation between the stem and the outer sleeve to alter longitudinal insertion of the stem into the outer sleeve when the relative rotation between the stem and the outer sleeve is within a predetermined range of altered rotation.

7. The prosthetic joint component of claim 6, wherein the sleeve interference protrusion defines at least one radially oriented altered rotation region longitudinally adjacent to the distal sleeve end and radially adjacent to an allowable rotation region, the allowable rotation region defining the predetermined range of allowable rotation and the altered rotation region defining the predetermined range of altered rotation.

8. A prosthetic joint component, comprising:
a joint articulating member including a joint articulating surface;
an anchor member configured for implantation into a native bone of a patient;
a chosen one of the joint articulating member and the anchor member including a stem, the stem configured for insertion into a stem-receiving cavity in the other one of the joint articulating member and the anchor member; and
at least one of the joint articulating member and the anchor member including a sleeve interference projection extending longitudinally therefrom; wherein
when the stem is inserted into the stem-receiving cavity with the joint articulating member implanted within the patient's body, the joint articulating member and the anchor member are configured for selective relative rotation about a shared longitudinal axis impelled by action of the patient, a portion of at least one of the joint articulating member and the anchor member impinges upon the sleeve interference protrusion responsive to a predetermined amount of relative rotation between the joint articulating member and the anchor member to prevent relative rotation between the joint articulating member and the anchor member outside a predetermined range of allowable rotation, and to alter longitudinal insertion of the stem into the stem-receiving cavity when the relative rotation between the joint articulating member and the anchor member is within a predetermined range of altered rotation.

9. The prosthetic joint component of claim 8, wherein the anchor member is an outer sleeve, the stem-receiving cavity is located in the outer sleeve, and the joint articulating member includes the stem.

10. The prosthetic joint component of claim 9, wherein the sleeve interference protrusion extends longitudinally from the anchor member.

11. The prosthetic joint component of claim 10, wherein the joint articulating member includes a joint articulating surface forming a portion of a prosthetic joint, the joint articulating surface being spaced from the stem by a connector neck, and the connector neck impinges upon the sleeve interference protrusion responsive to the predetermined amount of relative rotation between the joint articulating member and the anchor member.

12. The prosthetic joint component of claim 11, wherein the joint articulating surface forms a portion of at least one of a prosthetic hip joint, a prosthetic shoulder joint, a prosthetic ankle joint, a prosthetic knee joint, a prosthetic elbow joint, a prosthetic wrist joint, a prosthetic finger joint, a prosthetic toe joint, and a prosthetic spine component.

13. The prosthetic joint component of claim 8, wherein the sleeve interference protrusion defines a radially oriented allowable rotation region, the allowable rotation region defining the predetermined range of allowable rotation.

14. The prosthetic joint component of claim 8, wherein the predetermined range of permissible rotation is in the range of 30-60° of a full 360° relative rotation of the joint articulating member and the anchor member.

15. The prosthetic joint component of claim 8, wherein the sleeve interference protrusion defines at least one radially oriented altered rotation region radially adjacent to an allowable rotation region, the allowable rotation region defining the predetermined range of allowable rotation and the altered rotation region defining the predetermined range of altered rotation.

16. A method of regulating rotation of a prosthetic joint component, the method comprising the steps of:
providing an elongate, longitudinally oriented outer sleeve including an outer sleeve surface configured for implantation into native bone of a patient and having a sleeve body extending between longitudinally separated proximal and distal sleeve ends, a stem-receiving cavity extending from the distal sleeve end into the sleeve body substantially in a first longitudinal direction, the sleeve including a sleeve interference protrusion extending from the distal sleeve end away from the sleeve body substantially in a second longitudinal direction opposite the first longitudinal direction;
providing a joint articulating member including an elongate, longitudinally oriented stem with longitudinally spaced proximal and distal stem ends separated by a stem body, the proximal stem end being configured for selective insertion into the stem-receiving cavity, the joint articulating member including a joint articulating surface spaced apart from the distal stem end by an angularly extending connector neck;

implanting the outer sleeve and joint articulating member into the patient's body;

inserting at least a portion of the stem into the stem-receiving cavity;

relatively rotating the stem and the outer sleeve about a shared longitudinal axis, impelled by action of the patient;

impinging the connector neck upon the sleeve interference protrusion responsive to a predetermined amount of relative rotation between the stem and the outer sleeve; and preventing relative rotation between the stem and the outer sleeve outside a predetermined range of allowable rotation.

17. The method of claim 16, wherein the joint articulating surface forms a portion of at least one of a prosthetic hip joint, a prosthetic shoulder joint, a prosthetic ankle joint, a prosthetic knee joint, a prosthetic elbow joint, a prosthetic wrist joint, a prosthetic finger joint, a prosthetic toe joint, and a prosthetic spine component.

18. The method of claim 16, wherein the sleeve interference protrusion extends longitudinally from a majority of the distal sleeve end.

19. The method of claim 16, including the steps of:

defining a radially oriented allowable rotation region longitudinally adjacent to the distal sleeve end; and defining the predetermined range of allowable rotation with the allowable rotation region.

20. The method of claim 16, wherein the predetermined range of permissible rotation is in the range of 30-60° of a full relative rotation of the stem and the outer sleeve.

21. The method of claim 16, including the step of impinging the connector neck upon the sleeve interference protrusion responsive to a predetermined amount of relative rotation between the stem and the outer sleeve to alter longitudinal insertion of the stem into the outer sleeve when the relative rotation between the stem and the outer sleeve is within a predetermined range of altered rotation.

22. The method of claim 21, including the steps of:

defining a radially oriented allowable rotation region longitudinally adjacent to the distal sleeve end;

defining the predetermined range of allowable rotation with the allowable rotation region;

defining at least one radially oriented altered rotation region longitudinally adjacent to the distal sleeve end and radially adjacent to the allowable rotation region; and defining the predetermined range of altered rotation with the altered rotation region.

* * * * *